United States Patent [19]

Kirmann

[11] Patent Number: Plant 6,017

[45] Date of Patent: Sep. 22, 1987

[54] GERANIUM PLANT NAMED GYPSY

[75] Inventor: Wolfgang Kirmann, Langenzersdorf, Austria

[73] Assignee: Mirko Vavra, Bisamberg, Austria

[21] Appl. No.: 810,675

[22] Filed: Dec. 19, 1985

[51] Int. Cl.[4] ..... A01H 5/00

[52] U.S. Cl. ..... Plt./68

[58] Field of Search ..... Plt. 68

*Primary Examiner*—Robert E. Bagwill

*Attorney, Agent, or Firm*—Schwartz, Jeffery, Schwaab, Mack, Blumenthal & Evans

[57] ABSTRACT

A geranium plant named Gypsy having light pink flower color, variegated with deep purple; compact, self-branching growth habit; early flowering; good bud production at night temperatures up to 16° C., thus providing a long and continuous flowering period; and ease of propagation and good rooting habit.

2 Drawing Figures

The present invention comprises a new and distinct cultivar of geranium, botanically known as *Pelargonium domesticum,* and hereinafter referred to by the cultivar name Gypsy.

Gypsy is a product of a planned breeding program which had the objective of creating new geranium cultivars having compact growth habit, early flowering, good flower production, long flowering period, durable flowers, small foliage, and light pink flower color.

Gypsy was originated from a hybridization made by applicant in a controlled breeding program in Bisamberg, Austria in 1979. The female parent was a cultivar designated as seedling 24/78 having small foliage, excellent flower production and pale pink flower color. The male parent of Gypsy was Destiny 75, a white variety with a compact growth habit.

Gypsy was discovered and selected as one flowering plant within the progeny of the stated cross by applicant on Apr. 1, 1980 in a controlled environment in Bisamberg, Austria.

The first act of asexual reproduction of Gypsy was accomplished when vegetative cuttings were taken from the initial selection on Aug. 24, 1980 in a controlled environment in Bisamberg, Austria by a technician working under formulations established and supervised by Wolfgang Kirmann. Horticultural examination of selected units initiated in the spring of 1981 has demonstrated that the combination of characteristics as herein disclosed for Gypsy are firmly fixed and are retained through successive generations of asexual reproduction.

Gypsy has not been observed under all possible environmental conditions. The phenotype may vary significantly with variations in environment such as temperature, light intensity, and day length. The following observations, measurements and comparisons describe plants grown in Bisamburg, Austria under conditions which approximate those generally used in commercial practice.

The following traits have been repeatedly observed and are determined to be basic characteristics of Gypsy, which in combination distinguish this geranium as a new and distinct cultivar.

1. Light pink flower color; upper petals variegated with deep purple.
2. Propagates well, with very good rooting habit.
3. Small, relatively light green foliage.

4. Compact, self-branching growth habit, resulting in the setting of many buds, and floriferous flowering habit.
5. Early flowering and long flowering period.
6. Buds are produced under normal greenhouse conditions (5000 Lux for 16 hours per day) at 14°-16° C. This is well above the cooler temperatures required for previous *domesticum* varieties. In addition, plants flowered indoors can be transplanted outdoors and will continue blooming at night temperatures as high as 16° C. Known *domesticum* cultivars will produce buds outdoors only at night temperatures of 10° C. or lower.
7. Gypsy is unique with regard to the combined features of compactness, continuous flowering, floriferous habit, and light pink flower color.

Of the many commercial cultivars known to the present inventor, the most similar in comparison to Gypsy is Brilliant, an unpatented but commercial cultivar. In comparison to Brilliant, Gypsy has a more compact growth habit, smaller foliage, lighter pink flower color, and is earlier flowering.

The accompanying photographic drawings show typical flower and foliage characteristics of Gypsy, with colors being as true as possible with illustrations of this type.

Sheet 1 is a perspective view of a potted plant of Gypsy.

Sheet 2 is a black and white print showing the upper surface of immature and mature plants of Gypsy.

In the following description color references are made to The Royal Horticultural Society Colour Chart (RHS). The color values were determined at 9:00 a.m. on May 23, 1985 under 35,000 Lux light intensity in a greenhouse at Hillscheid, Federal Republic of Germany.

Classification:

*Botanical.*—*Pelargonium domesticum.*

*Commercial.*—Commonly referred to as a "Martha Washington" geranium, and having the cultivar name Gypsy.

INFLORESCENCE

A. Umbel:

*Average diameter.*—Relatively small, 85–95 mm.

*Peduncle length.*—Normal.

*Pedicel length.*—Normal.

B. Corolla:

*Average diameter.*—55–65 mm; floriferous habit results in total inflorescence diameter extending at least to periphery of foliage.

*Form.*—Five-six petals.

*Color (general tonality from a distance of three meters).*—Pale lavender-pink, with dark purple variegation on upper two petals.

*Color (upper surface).*—65B,C,D; upper petals variegated with 60B and deeper 60A at center of variegation.

C. Bud:

*Shape.*—Elongated.

*Color.*—Light pink.

D. Reproductive organs:

*Androecium.*—Yellow-red.

*Gynoecium.*—Five to seven part.

E. Spring flowering response period: Early.

F. Durability: Very good.

PLANT

A. Foliage:

*Form.*—Zygomorphic with a nectar spur.

*Margin.*—Crenate and indented.

*Color (upper surface).*—Light green.

*Tolerance of botrytis and soil fungi.*—Excellent, except under conditions of very high humidity.

B. General appearance and form:

*Internode length.*—Very short.

*Branching pattern.*—Excellent.

*Height.*—Compact.

I claim:

1. A new and distinct cultivar of geranium named Gypsy, as described and illustrated, and particularly characterized by its light pink flower color, variegated with deep purple; compact self-branching growth habit; early flowering; good bud production at night temperatures up to 16° C., thus providing a long and continuous flowering period; and ease of propagation and good rooting habit.

* * * * *

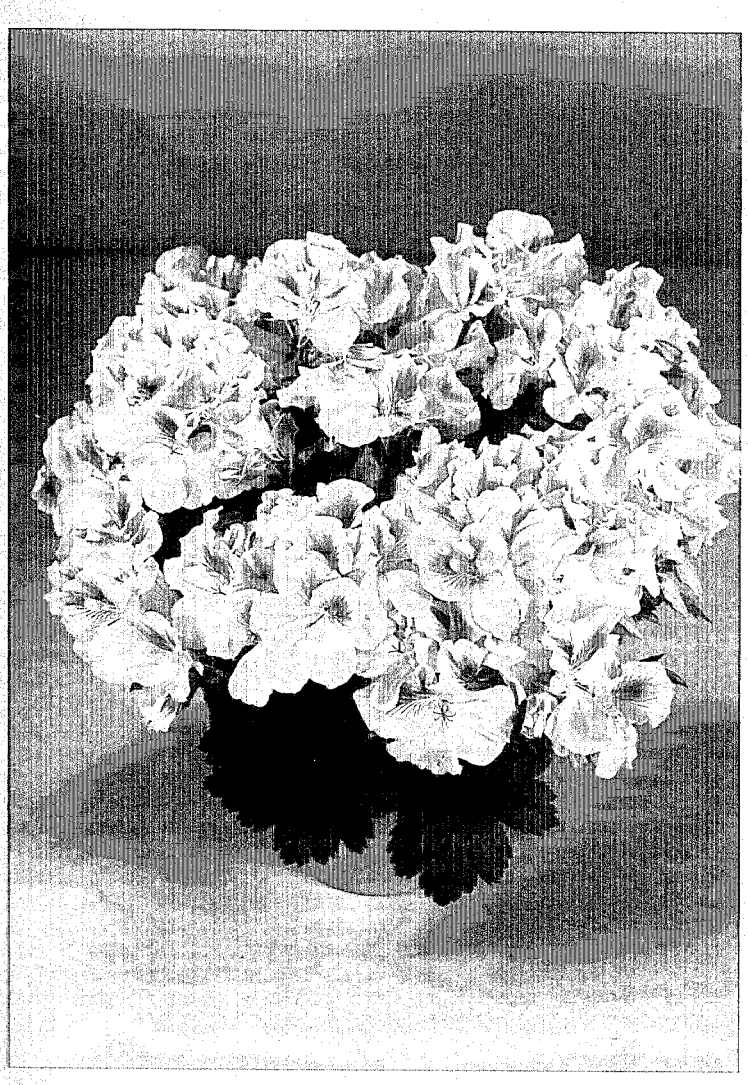

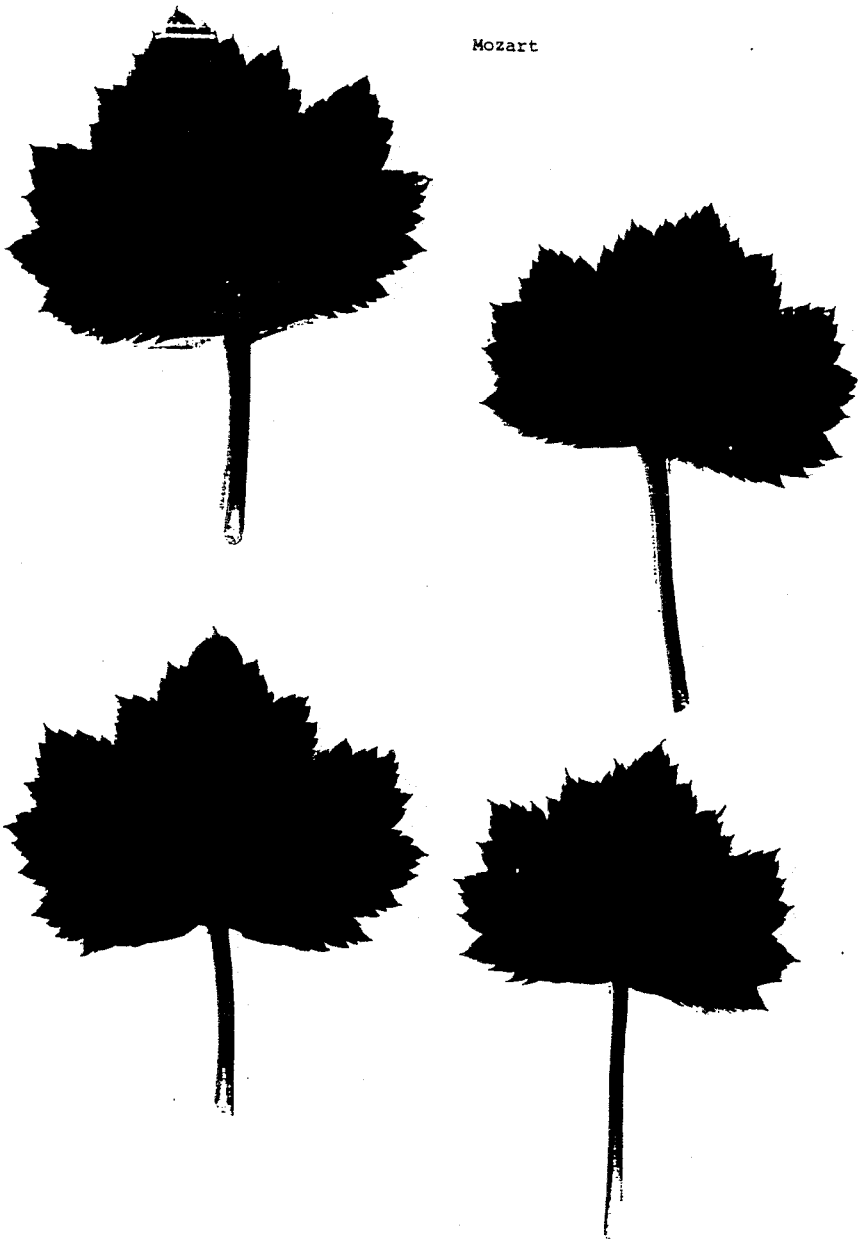
Mozart